United States Patent [19]

Schriewer et al.

[11] Patent Number: 4,705,788
[45] Date of Patent: Nov. 10, 1987

[54] NOVEL ANTIBACTERIAL 7-AMINO-1(SUBSTITUTED CYCLOPROPYL)-1,4-DIHYDRO-4-OXO-3-QUINOLINECARBOXYLIC ACIDS

[75] Inventors: Michael Schriewer, Leverkusen; Klaus Grohe, Odenthal; Hans-Joachim Zeiler, Velbert; Karl G. Metzger, Wuppertal, all of Fed. Rep. of Germany

[73] Assignee: Bayer Aktiengesellschaft, Leverkusen, Fed. Rep. of Germany

[21] Appl. No.: 834,170

[22] Filed: Feb. 27, 1986

[30] Foreign Application Priority Data

Mar. 16, 1985 [DE] Fed. Rep. of Germany ....... 3509546

[51] Int. Cl.$^4$ .................. A61K 31/495; C07D 401/04
[52] U.S. Cl. .................................... 514/254; 514/222; 514/236; 544/62; 544/128; 544/363; 546/156; 564/1
[58] Field of Search .......................... 544/363, 62, 128; 514/254, 222, 236; 546/156

[56] References Cited

U.S. PATENT DOCUMENTS

| 4,448,962 | 5/1984 | Irikura et al. | 544/362 |
| 4,544,658 | 10/1985 | Petersen et al. | 544/363 |
| 4,556,658 | 12/1985 | Grohe et al. | 544/363 |
| 4,563,459 | 1/1986 | Grohe et al. | 544/363 |
| 4,588,726 | 5/1986 | Petersen et al. | 544/363 |

FOREIGN PATENT DOCUMENTS 0106489 4/1984 European Pat. Off.
3306771 8/1984 Fed. Rep. of Germany ...... 544/363

OTHER PUBLICATIONS

Chemical Abstracts, vol. 93, Nov. 24, 1980, No. 21–Abstract No. 198 382n, Koga et al., "Structure–activity Relationships of Antibacterial 6,7- and 7,8-Disubstituted 1-Alkyl-1,4-Dihydro-4-Oxo-Quinoline-3-Carboxylic Acids".
Chemical Abstracts, vol. 98, Jan. 17, 1983, No. 3–Abstract No. 16037b, Lebedev et al., "Quantum–chemical Study of the Electronic Structure of Chlorocyclopropanes and Hydrogenolysis of Carbonchlorine Bonds in Gem–Dichlorocyclopropanes".
Chemical Abstracts, vol. 96, Mar. 15, 1982, No. 11–Abstract No. 85585z, Kyorin Pharmaceutical Co., Ltd., "Piperazinoquinolonecarboxylic Acid Derivatives".
Chemical Abstracts, vol. 102, Jan. 21, 1985, No. 3–Abstract No. 24503s, Irikura, et al., "Quinolinecarboxylic Acid Derivatives".

Primary Examiner—Glennon H. Hollrah
Assistant Examiner—James H. Turnipseed
Attorney, Agent, or Firm—Sprung Horn Kramer & Woods

[57] ABSTRACT

Novel antibacterially active 7-amino-1-(substituted cyclopropyl)-1,4-dihydro-4-oxo-3-quinolinecarboxylic acids of the formula

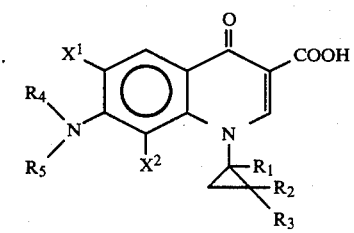

in which
$X^1$ and $X^2$ can be identical or different and represent hydrogen or halogen,
$R_1$, $R_2$ and $R_3$ represent hydrogen, methyl, chlorine or fluorine, the radicals $R_1$–$R_3$ never all being identical, and
$R^4$ and $R^5$, together with the nitrogen atom to which they are bonded, form a 5-membered or 6-membered heterocyclic ring which may be substituted.

13 Claims, No Drawings

NOVEL ANTIBACTERIAL 7-AMINO-1(SUBSTITUTED CYCLOPROPYL)-1,4-DIHYDRO-4-OXO-3-QUINOLINECARBOXYLIC ACIDS

The present invention relates to new 7-amino-1-(substituted cyclopropyl)-1,4-dihydro-4-oxo-3-quinolinecarboxylic acids, processes for their preparation and antibacterial agents containing these compounds.

The new 7-amino-1-(substituted cyclopropyl)-1,4-dihydro-4-oxo-3-quinolinecarboxylic acids of the formula (I)

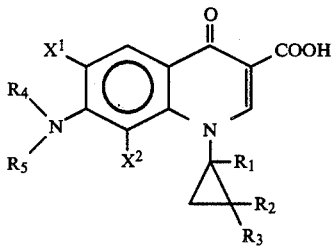

in which
$X^1$ and $X^2$ can be identical or different and represent hydrogen or halogen, in particular chlorine or fluorine, $R_1$, $R_2$ and $R_3$ represent hydrogen, methyl, chlorine or fluorine, the radicals $R_1$–$R_3$ never all being identical, and $R_4$ and $R_5$, together with the nitrogen atom to which they are bonded, form a 5-membered or 6-membered heterocyclic ring which can additionally contain, as a ring member, the atoms or groups —O—, —S—, —SO—, —SO$_2$—, >N—R$^6$ or

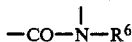

and which can optionally be mono-, di- or tri-substituted on the carbon atoms by $C_1$–$C_4$-alkyl, by phenyl or cyclohexyl which is optionally mono-, di- or tri-substituted by chlorine, fluorine, bromine, methyl, phenyl, hydroxyl, methoxy, benzyloxy, nitro or piperidino, or by 2-thienyl, hydroxyl, alkoxy with 1 to 3 carbon atoms, amino, methylamino or ethylamino,
wherein
R$^6$ represents hydrogen, or represents a branched or straight-chain alkyl, alkenyl or alkinyl group which has 1 to 6 carbon atoms and can optionally be substituted by one or two hydroxyl, alkoxy, alkylamino or dialkylamino groups with 1 to 3 carbon atoms in each alkyl radical, the cyano group or the alkoxycarbonyl group with 1 to 4 carbon atoms in the alcohol part, or represents a phenylalkyl group which is optionally substituted in the phenyl radical and has up to 4 carbon atoms in the aliphatic part, or represents a phenacyl radical which is optionally mono- or di-substituted by hydroxyl, methoxy, chlorine or fluorine, or represents an oxoalkyl radical with up to 6 carbon atoms, or furthermore denotes a radical COR$^7$, CN or SO$_2$R$^8$,
wherein
R$^7$ represents hydrogen, or represents straight-chain or branched alkyl which has 1 to 4 carbon atoms and is optionally substituted by 1 or 2 substituents from the series comprising amino, alkoxycarbonyl with 1 to 3 carbon atoms in the alkyl part, carboxyl and alkoxy with 1 to 3 carbon atoms and halogen, such as chlorine, bromine and fluorine, or represents alkoxy with 1 to 4 carbon atoms, amino or alkylamino or dialkylamino with 1 to 5 carbon atoms in the alkyl part and
R$^8$ represents straight-chain or branched alkyl with 1 to 3 carbon atoms,
and pharmaceutically usable hydrates, acid addition salts and alkali metal, alkaline earth metal and guanidinium salts thereof, which have a powerful antibacterial action, have been found.

These compounds are therefore suitable as active compounds for human and veterinary medicine, veterinary medicine also including the treatment of fish for the therapy or prevention of bacterial infections.

Preferred compounds of the formula (I) are those in which
$X^1$ and $X^2$ can be identical or different and represent hydrogen, chlorine or fluorine $R_1$, $R_2$ and $R_3$ represent halogen, methyl, chlorine and fluorine, all the radicals $R_1$–$R_3$ never being identical, and
$R_4$ and $R_5$, together with the nitrogen atom to which they are bonded, can form a 5-membered or 6-membered heterocyclic ring which can additionally contain, as a ring member, the atoms or groups —O—, —S—, —SO$_2$—, N—R$^6$ or

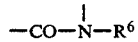

and which can optionally be mono- or di-substituted on the carbon atoms by $C_1$–$C_3$-alkyl or cyclohexyl, or by phenyl which is optionally mono- or disubstituted by chlorine, fluorine, bromine, methyl, phenyl, hydroxyl, methoxy, benzyloxy, nitro or piperidino, or by 2-thienyl, hydroxyl, amino or methylamino,
wherein
R$_6$ represents hydrogen, or represents a branched or straight-chain alkyl, alkenyl or alkinyl group which has up to 4 carbon atoms and can optionally be substituted by one or two hydroxyl groups, or represents a phenacyl radical or an oxoalkyl radical with up to 5 carbon atoms, or represents a radical COR$^7$,
wherein
R$^7$ denotes hydrogen, straight-chain or branched alkyl with 1 to 3 carbon atoms, alkoxy with 1 to 3 carbon atoms, amino, or alkylamino or dialkylamino with 1 to 3 carbon atoms in each alkyl part.

Particularly preferred compounds of the formula (I) are those in which
$X^1$ and $X^2$ can be identical or different and represent hydrogen, chlorine or fluorine,
$R_1$, $R_2$ and $R_3$ represent hydrogen, methyl, chlorine or fluorine, all the radicals $R_1$–$R_3$ never being identical, and
R$^4$ and R$^5$, together with the nitrogen atom to which they are bonded, can form a 5-membered or 6-membered heterocyclic ring which can additionally contain, as a ring member, an oxygen atom or the groups N—R$^6$ or

and which can optionally be mono- or di-substituted on the carbon atom by $C_1$-$C_2$-alkyl or cyclohexyl, or by phenyl which is optionally substituted by chlorine, fluorine, methyl, phenyl, hydroxyl, methoxy, benzyloxy, nitro or piperidino, or by 2-thienyl or hydroxyl,
wherein
  $R^6$ represents hydrogen, or represents a branched or straight-chain alkyl group which has 1 to 3 carbon atoms and can optionally be substituted by one or two hydroxyl groups, or represents a phenacyl radical or an oxoalkyl radical with up to 4 carbon atoms, or represents a radical $COR^7$,
wherein
  $R^7$ denotes hydrogen or alkyl with one or two carbon atoms.

It has furthermore been found that the compounds of the formula (I) are obtained by a process in which the 1-(substituted cyclopropyl)-7-halogen-1,4-dihydro-4-oxo-3-quinolinecarboxylic acids of the formula (II)

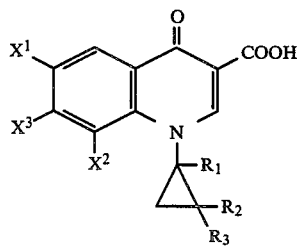

(II)

in which
  $X^1$ and $X^2$ have the abovementioned meaning and
  $X^3$ represents halogen, preferably chlorine or fluorine,
are reacted with amines of the formula (III)

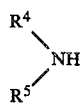

(III)

in which $R_4$ and $R_5$ have the abovementioned meaning, if appropriate in the presence of acid-binding agents (method A.)

Compounds of the formula (I) according to the invention can also be obtained by a process in which a 7-(1-piperazinyl)-3-quinolonecarboxylic acid of the formula (IV)

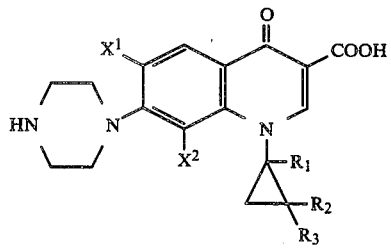

(IV)

in which $X^1$ and $X^2$ have the abovementioned meaning and the piperazinyl radical can be mono- di- or trisubstituted on its carbon atoms by $C_1$-$C_4$-alkyl, 2-thienyl or optionally substituted cyclohexyl or phenyl,
is reacted with compounds of the formula (V)

$$R^6X \qquad (V)$$

in which
  $R^6$ has the abovementioned meaning, but cannot be hydrogen, and
  X denotes fluorine, chlorine, bromine, iodine, hydroxyl, acyloxy, ethoxy, phenoxy or 4-nitrophenoxy,
if appropriate in the presence of acid-binding agents (method B).

Compounds of the formula (I) according to the invention are also obtained by the process in which a 7-(1-piperazinyl)-3-quinolonecarboxylic acid of the formula (IV) in which the piperazinyl radical can be mono-, di- or tri-substituted on its carbon atoms by $C_1$-$C_4$-alkyl, 2-thienyl or optionally substituted cyclohexyl or phenyl is reacted with Michael acceptors of the formula (VI)

$$B-CH=CH_2 \qquad (VI)$$

in which
  B represents CN, $CO-R^9$ or $COOR^{10}$,
wherein
  $R^9$ represents methyl or ethyl and
  $R^{10}$ represents methyl, ethyl or n- or i-propyl,
(method C).

If 2-methylpiperazine and 7-chloro-6-fluoro-1,4-dihydro-1-(1-methylcyclopropyl)-4-oxo-3-quinolinecarboxylic acid are used as starting substances in the reaction according to method A, the course of the reaction can be represented by the following equation:

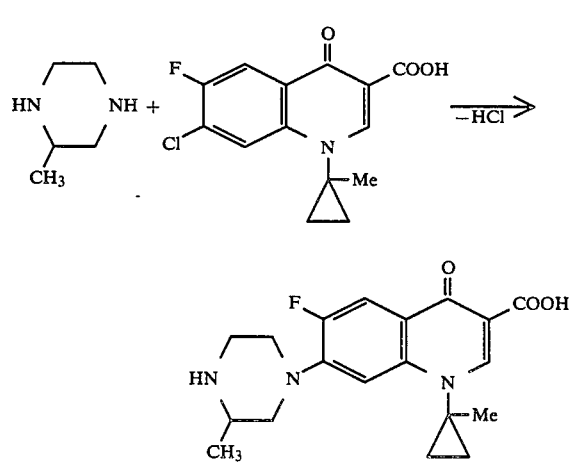

If ethyl iodide and 6-fluoro-1,4-dihydro-1-(1methyl-cyclopropyl)-4-oxo-7-(1-piperazinyl)-3-quinolinecarboxylic acid are used as starting substances in the reaction according to method B, the course of the reaction can be represented by the following equation:

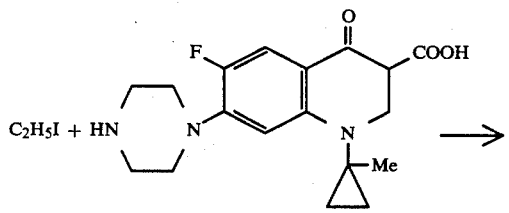

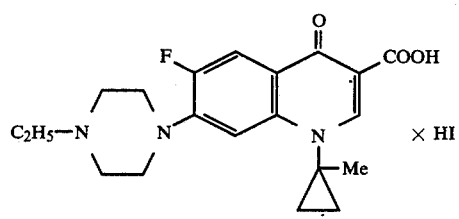

If, for example, 6-fluoro-1, 4-dihydro-1-(1-methylcyclopropyl)-7-(1-methylpiperazinyl)-4-oxo-3-quinolinecarboxylic acid and formic/acetic anhydride are used as starting compounds in the reaction of (IV) with (V) according to method B, the course of the reaction can be represented by the following equation:

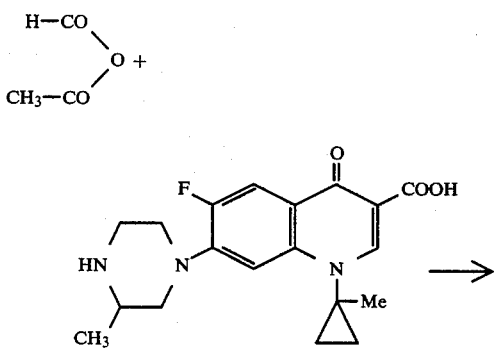

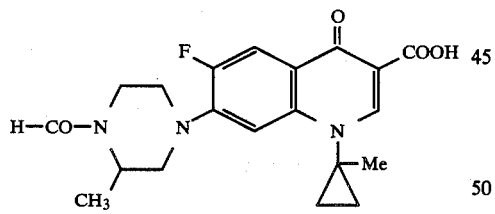

If, for example, 6-fluoro-1, 4-dihydro-1-(1-methylcyclopropyl)-4-oxo-7-(1-piperazinyl)-3-quinolinecarboxylic acid and methyl vinyl ketone are used as starting compounds according to method C, the course of the reaction can be represented by the following equation:

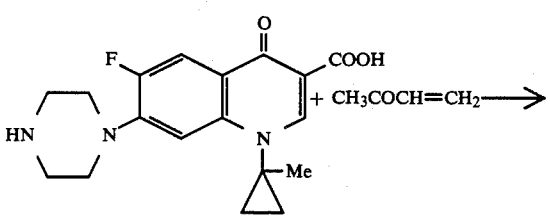

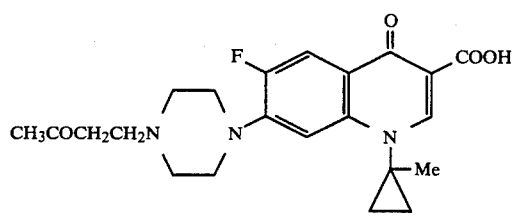

The 1-cyclopropyl-6,7,8-trihalogeno-1, 4-dihydro-4-oxo-3-quinolinecarboxylic acids of the formula (II) which can be used as starting substances according to method A can be prepared in accordance with the following equation

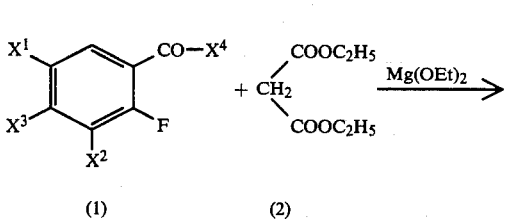

$X^4 = F$ or $Cl$

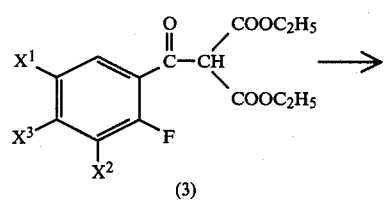

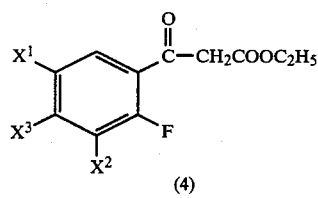

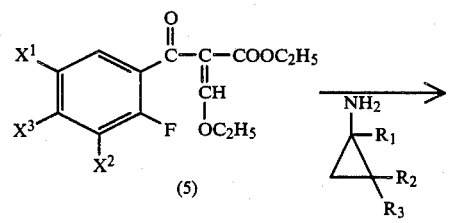

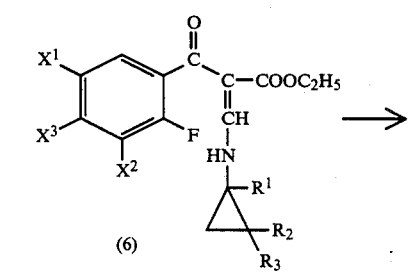

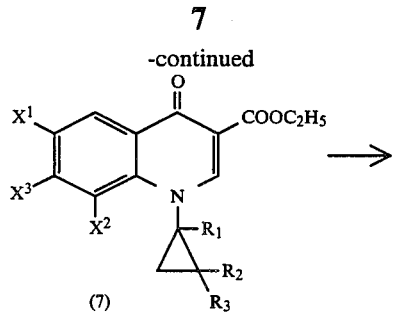

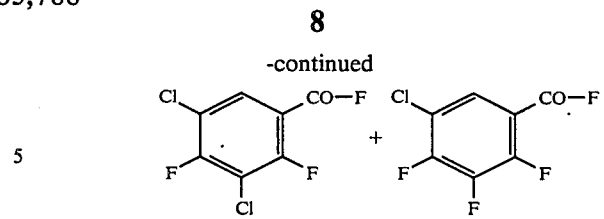

According to this equation, diethyl malonate (2) is acylated with the corresponding benzoyl fluoride of chloride (1) in the presence of magnesium ethylate to give the aroylmalonate (3) (Organicum, 3rd edition 1964, page 438).

Partial hydrolysis and decarboxylation of (3) in an aqueous medium with catalytic amounts of sulphuric acid or p-toluenesulphonic acid gives a good yield of the ethyl aroylacetate (4), which is converted into ethyl 2-(2,3,4,5-tetrahalogenobenzoyl)-3-ethoxy-arcylate (5) with triethyl orthoformate/acetic anhydride. The reaction of (5) with the corresponding substituted cyclopropylamine in a solvent, such as, for example, methylene chloride, alcohol, chloroform, cyclohexane or toluene, gives the desired intermediate product (6) in a slightly exothermic reaction.

The cyclization reaction (6)→(7) is carried out in a temperature range from about 60 to 300° C., preferably 80° to 180° C.

Diluents which can be used are dioxane, dimethylsulphoxide, N-methylpyrrolidone, sulpholane, hexamethylphosphoric acid triamide and, preferably, N,N-dimethylformamide.

Possible acid-binding agents for this reaction stage are potassium tert.-butanolate, butyl-lithium, lithiumphenyl, phenyl-magnesium bromide, sodium methylate, sodium hydride and sodium or potassium carbonate, and particularly preferably potassium fluoride or sodium fluoride. It may be advantageous to employ an excess of 10 mol % of base.

The benzoyl halides required as starting substances for this synthesis route are prepared as follows:

3,5-Dichloro-2,4-difluoro-benzoyl fluoride (boiling point 97°/20 mbar; $n_D^{20} = 1.5148$) and 5-chloro-2,3,4-trifluorobenzoyl fluoride (boiling point 66-70°/20 mbar; $n_D^{20} = 1.4764$) are obtained side by side by heating tetrachlorobenzoyl chloride to elevated temperatures with potassium fluoride in sulpholane:

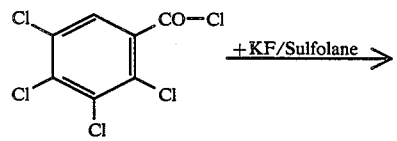

Chlorination of 2,4,5-trifluorobenzoic acid in chlorosulphonic acid gives 3-chloro-2,4,5-trifluorobenzoic acid, which is reacted as the crude product with thionyl chloride to give 3-chloro-2,4,5-trifluorobenzoyl chloride (boiling point 94°/18 mbar; n20 = 1.5164):

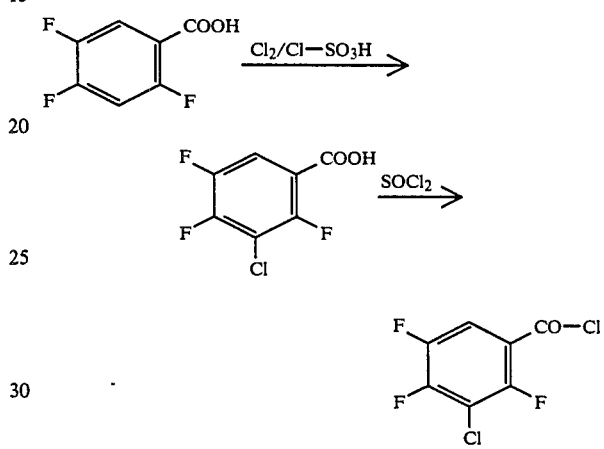

The ester hydrolysis of (7) which takes place in the last step under basic or acid conditions gives the 1-(substituted cyclopropyl)-1,4-dihydro-4-oxo-3-quinolinecarboxylic acids.

Some of the cyclopropylamines required as starting substances are known.

The 1-amino-2,2-difluorocyclopropane employed has prepared as follows:

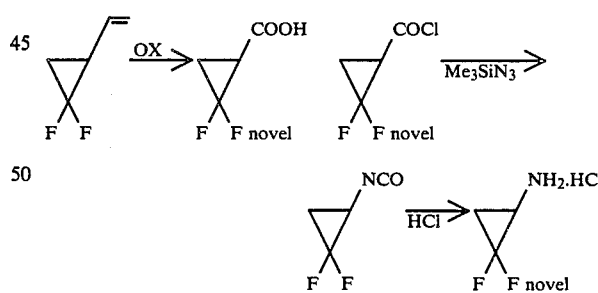

(a) 2,2-Difluorocyclopropanecarboxylic acid 20.8 g of 2,2-difluorovinylcyclopropane are introduced into 220 ml of water. 96 g of finely powdered KMnO₄ are added in portions to the well-stirred emulsion such that the temperature does not exceed 35° C. After the mixture has been stirred for one hour, the MnO₂ is filtered off. NaHSO₃ is added to the mother liquor until decoloration has occurred. The mixture is then acidified with dilute H₂SO₄. The mixture is extracted with Et₂O and the organic phase is separated off, dried and concentrated.

(b) 1-Amino-2,2-difluorocyclopropanecarboxylic acid hydrochloride 18 g of difluorocyclopropanecarboxylic acid and 32.7 ml of $SOCl_2$ are boiled for 2 hours. Thereafter, the excess thionyl chloride is distilled off. 10 g of the residue are added dropwise to a solution of 19.5 g of $Me_3SiN_3$ in 42 ml of toluene. The mixture is heated to 60-80° C. until no further gas is formed.

60 ml of concentrated HCl are added at room temperature. The two phases are shaken until no further gas is formed. The aqueous phase is separated off and concentrated in vacuo.

Yield: 5.1 g

1-Amino-2,2-dichlorocyclopropane hydrochloride is obtained from 2,2-dichlorocyclopropanoic acid by the same method.

The amines (III) used as starting substances are known or can be obtained by processes which are known from the literature [U.S. Pat. No. 4,166,180 and J. Med. Chem. 26, 1116 (1983)]. The corresponding 2-cyclohexyl-piperazines are obtained from the 2-arylpiperazines by catalytic hydrogenation; for example: 2-cyclohexyl-piperazine (waxy, melting point 71°-73° C.). Examples which may be mentioned are: morpholine, piperidine, thiomorpholine, pyrrolidine, piperazine, N-methylpiperazine, N-ethylpiperazine, N-(2-hydroxyethyl)-piperazine, N-formylpiperazine, 2-methylpiperazine, 1,2-dimethylpiperazine, cis- and trans-2,5-dimethylpiperazine, cis- and trans-2,6-dimethylpiperazine, 2-ethylpiperazine, 2-propylpiperazine, 2-isopropylpiperazine, 2-isobutylpiperazine, 2-piperazinone, 1-methyl-2-piperazinone, 1-ethyl-2-piperazinone, 2-cyclohexylpiperazine, 2-phenylpiperazine, 2-(4-chlorophenyl)-piperazine, 2-(4-fluorophenyl)-piperazine, 2-(4-bromophenyl)-piperazine, 2-(4-methylphenyl)-piperazine, 2-(4-biphenyl)-piperazine, 2-(4-methoxyphenyl)-piperazine, 2-(4-benzyloxyphenyl)piperazine, 2-(4-hydroxyphenyl)-piperazine, 2-(4-nitrophenyl)-piperazine, 2-(3-nitrophenyl)-piperazine, 2-(4-piperidinophenyl)-piperazine, 2-(3,4-dimethoxyphenyl)-piperazine, 2-(3,4,5-trimethoxyphenyl)-piperazine, 2-(3,4-dimethoxy- 6-methyl)-piperazine, 2-(2-thienyl)-piperazine and 3-aminopyrrolidine.

The compounds of the formula (V) used as starting substances are known. Examples which may be mentioned are: methyl iodide, methyl bromide, ethyl iodide, ethyl bromide, ethyl chloride, 2-hydroxyethyl chloride, 3-hydroxypropyl chloride, 4-hydroxybutyl chloride, n-propyl bromide, i-propyl iodide, n-butyl bromide, i-butyl bromide, sec.-butyl chloride, n-pentyl chloride, 3-methylbutyl chloride and n-hexyl bromide; as well as formic acetic anhydride, acetic anhydride, propionic anhydride, acetyl chloride, chloroacetyl chloride, dichloroacetyl chloride, bromoacetyl bromide, butyryl chloride, 4-chlorobutyryl chloride, isobutyryl chloride, N-(tert.-butoxycarbonylglycine 4-nitrophenyl ester, N-(tert.-butoxycarbonyl)-L-alanine 4-nitro-phenyl ester, N-(tert.-butoxycarbonyl)-L-leucine 4-nitro-phenyl ester, N-(tert.-butoxycarbonyl)-L-valine 4-nitro-phenyl ester, 3methoxypropionyl chloride, methyl chlorocarbonate, ethyl chlorocarbonate, n-butyl chlorocarbonate, diethyl carbonate, cyanogen chloride, diphenyl carbonate, cyanogen bromide, dimethylcarbamyl chloride, methanesulphonyl chloride, ethanesulphonyl chloride, propane-1-sulphonyl chloride and formic acid.

The compounds of the formula (VII) which can be used according to the invention are known. Examples which may be mentioned are: acrylonitrile, methyl vinyl ketone, methyl acrylate and ethyl acrylate.

The reaction of (II) with (III) according to method A is preferably carried out in a diluent, such as dimethylsulphoxide, N,N-dimethylformamide, hexamethylphosphoric acid trisamide, sulpholane, water, an alcohol, such as methanol, ethanol, n-propanol or isopropanol, glycol monomethyl ether or pyridine. Mixtures of these diluents can also be used.

All the usual inorganic and organic acid-binding agents can be used as the acid-binding agents. These include, preferably, the alkali metal hydroxides, alkali metal carbonates, organic amines and amidines. Specific examples which may be mentioned as particularly suitable are: triethylamine, 1,4-diaza-bicycloL2,2,2-octane (DABCO), 1,8-diaza-bicycloL5,4,0j-undec-7-ene(DBU) or excess amine (III).

The reaction temperatures can be varied within a substantial range. In general, the reaction is carried out between about 20 and 200° C., preferably between 80 and 180° C.

The reaction can be carried out under normal pressure, but also under increased pressure. In general, the reaction is carried out under pressures between about 1 and about 100 bar, preferably between 1 and 10 bar.

In carrying out the process according to the invention, 1 to 15 moles, preferably 1 to 6 moles, of the amine (III) are employed per mole of the carboxylic acid (II).

The reaction of (IV) with (V) is preferably carried out in the presence of a diluent, such as dimethylsulphoxide, dioxane, N,N-dimethylformamide, hexamethylphosphoric acid trisamide, sulpholane, water, an alcohol, such as methanol, ethanol, n-propanol or isopropanol, glycol monomethyl ether or pyridine. Mixtures of these diluents can also be used.

All the usual inorganic and organic acid-binding agents can be used as the acid-binding agents. These include, preferably, the alkali metal hydroxides, alkali metal carbonates, organic amines and amidines. Specific examples which may be mentioned as being particularly suitable are: triethylamine, 1,4-diazabicyclo12,2,2]octane (DABCO) or 1,8-diazabicyclo-[5,4,0]undec-7-ene (DBU).

The reaction temperatures can be varied within a substantial range. In general, the reaction is carried out between about 20 and about 180° C., preferably between 40 and 110° C.

The reaction can be carried out under normal pressure, but also under increased pressure. In general, the reaction is carried out under pressures between about 1 and about 100 bar, preferably between 1 and 10 bar.

In carrying out the process according to the invention by method B, 1 to 4 moles, preferably 1 to 1.5 moles, of the compound (V) are employed per mole of the compound (IV).

The reaction of (IV) with (VI) (method C) is preferably carried out in a diluent, such as dioxane, dimethylsulphoxide, N,N-dimethylformamide, methanol, ethanol, isopropanol, n-propanol or glycol monomethyl ether, or in mixtures of these diluents.

The reaction temperatures can be varied within a substantial range. In general, the reaction is carried out between about 20° C. and about 150° C., preferably between 50° C. and 100° C.

The reaction can be carried out under normal pressure, but also under increased pressure. In general, the reaction is carried out under pressures between about 1 and about 100 bar, preferably between 1 and 10 bar.

In carrying out the process according to the invention by method C, 1 to 5 moles, preferably 1 to 2 moles, of the compound (VI) are employed per mole of the compound (IV).

New active compounds which may be mentioned specifically, in addition to the compounds listed in the examples, are: 8-chloro-6-fluoro-1,4-dihydro-1-(1-methylcyclopropyl)-4-oxo-7-(1-piperazinyl)-3-quinolinecarboxylic acid, 6-chloro-8-fluoro-1,4-dihydro-1-(1-methylcyclopropyl)-4-oxo-7-(1-piperazinyl)-3-quinolinecarboxylic acid, 6-chloro-8-fluoro-1-(2,2-difluorocyclopropyl)-1,4-dihydro-4-oxo-7-(1-piperazinyl)-3-quinolinecarboxylic acid, 6,8-di-fluoro-1-(2-fluorocyclopropyl)-1,4-dihydro-4-oxo-7-(1-piperazinyl)-3-quinolinecarboxylic acid, 1-(2,2-dichlorocyclopropyl)-6,8-difluoro-1,4-dihydro-4-oxo-7-(1-piperazinyl)- 3-quinolinecarboxylic acid, 8-chloro-6-fluoro-1,4-dihydro-1-(2-methylcyclopropyl)-7-(3-methyl-1-piperazinyl)-4-oxo-3-quinolinecarboxylic acid, 8-chloro-6-fluoro-1,4-dihydro-1-(1-methylcyclopropyl)-7-(3-methyl-1-piperazinyl)-4-oxo-3-quinolinecarboxylic acid, 6-chloro-8-fluoro-1-(2-fluorocyclopropyl)-1,4-dihydro-4-oxo-7-(1-piperazinyl)-3-quinolinecarboxylic acid, 1-(2-chlorocyclopropyl)-6,8-difluoro-1,4-dihydro-4-oxo-7-(1-piperazinyl)-3-quinolinecarboxylic acid, 6,8-difluoro-1,4-dihydro-1-(1-methylcyclopropyl)-4-oxo-7-(3-phenyl-1-piperazinyl)-3-quinolinecarboxylic acid, 8-chloro-6-fluoro-1,4-dihydro-1-(1-methylcyclopropyl)-4-oxo-7-(3-phenyl-1-piperazinyl)-3-quinolinecarboxylic acid, 6,8-difluoro -1-(2,2-difluorocyclopropyl)-1,4-dihydro-4-oxo-7-(3-phenyl-1-piperazinyl)-3-quinolinecarboxylic acid, 8-chloro-6-fluoro-1-(2,2-difluorocyclopropyl)-1,4-dihydro-7-(4-methyl-1-piperazinyl)-4-oxo-3-quinolinecarboxylic acid, 6-chloro-8-fluoro-1-(2,2-difluorocyclopropyl)-1,4-dihydro-7-(4-methyl-1-piperazinyl)-4-oxo-3-quinolinecarboxylic acid, 7-(4-acetyl-1-piperazinyl)-6,8-difluoro-1,4-dihydro-1-(1-methylcyclopropyl)-4-oxo-3-quinolinecarboxylic acid, 6,8-difluoro-1,4-dihydro-4-oxo-7-14-(3-oxo-butyl)-1-piperazinylj-3-quinolinecarboxylic acid and 1-(2,2-dichlorocyclopropyl)-6-fluoro-1,4-dihydro-4-oxo-7-(1-piperazinyl)-3-quinolinecarboxylic acid The compounds according to the invention exhibit, with a low toxicity, a broad antibacterial spectrum against Gram-positive and Gram-negative germs, in particular against Enterobacteriaceae; and above all also against those which are resistant towards various antibiotics, such as, for example, penicillins, cephalosporins, aminoglycosides, sulphonamides and tetracyclines.

These useful properties enable them to be used as chemotherapeutic active compounds in medicine and as substances for preserving inorganic and organic materials, in particular all types of organic materials, for example polymers, lubricants, paints, fibers leather, paper and wood, and foodstuffs and water.

The compounds according to the invention are active against a very broad spectrum of microorganisms. With their aid it is possible to combat Gram-positive and Gram-negative bacteria and bacteria-like microorganisms and to prevent, alleviate and/or cure the diseases caused by these pathogens.

The compounds according to the invention are particularly active against bacteria and bacteria-like microorganisms. They are therefore particularly suitable, in human and veterinary medicine, for the prophylaxis and chemotherapy of local and systemic infections caused by the pathogens:

Gram-positive cocci, for example Staphylococci (*Staph. aureus* and *Staph. epidermidis*) and Streptococci (*Strept. agalactiae, Strept. faecalis, Strept. pneumoniae* and *Strept. pyogenes*); Gram-negative cocci (*Neisseria gonorrheae*) and Gram-negative rod-shaped bacilli, such as Enterobacteriaceae, for example *Escherichia coli, Haemophilus influenzae*, Citrobacter (*Citrob. freundii* and *Citrob. diverms*), Salmonella and Shigella; and furthermore Klebsiellae (*Klebsiella pneumoniae* and *Klebs. oxytoca*), Enterobacter (*Ent. aerogenes* and *Ent. agglomerans*), Hafnia Serratia (*Serr. mascescens*), Proteus (*Pr. nurabilis, Pr. rettgeri* and *Pr. vulgaris*) Providencia, Yersinia and the genus Acinetobacter. The antibacterial spectrum moreover includes the genus Pseudomonas (*Ps. aeruginosa* and *Ps. maltophilia*) as well as strictly anaerobic bacteria, such as, for example, *Bacteroides fragilis*, representatives of the genus Peptococcus, Peptostreptococcus and the genus Clostridium; and furthermore Mycoplasma (*M. pneumoniae, M.hominis* and *M.urealyticum*) and mycobacteria, for example *Mycobacterium tuberculosis*.

The above list of pathogens is purely illustrative and is in no way to be interpreted as restrictive. Examples which may be mentioned of diseases which can be prevented, alleviated and/or cured by the compounds according to the invention are: otitis; pharyngitis; pneumonia; peritonitis; pyelonephritis; cystitis; endocarditis; osteomyelitis; bronchitis; arthritis; local infections; and septic diseases.

The present invention includes pharmaceutical formulations which, in addition to non-toxic, inert pharmaceutically suitable excipients, contain one or more compounds according to the invention or which consist of one or more compounds according to the invention, as well as processes for the preparation of these formulations.

The present invention also includes pharmaceutical formulations in dosage units. This means that the formulations are in the form of individual parts, for example tablets, dragees, capsules, pills, suppositories and ampoules, the active compound content of which corresponds to a fraction or a multiple of an individual dose. The dosage units can contain, for example, 1, 2, 3 or 4 individual doses or $\frac{1}{2}$, $\frac{1}{3}$ or $\frac{1}{4}$ of an individual dose. An individual dose preferably contains the amount of active compound which is given in one administration and which usually corresponds to a whole, a half, one third or one quarter of a daily dose.

By non-toxic, inert pharmaceutically suitable excipients there are to be understood solid, semi-solid or liquid diluents, fillers and formulation auxiliaries of every kind.

Tablets, dragees, capsules, pills, granules, suppositories, solutions, suspensions and emulsions, pastes, ointments, gels, creams, lotions, powders and sprays may be mentioned as preferred pharmaceutical formulations.

Tablets, dragees, capsules, pills and granules can contain the active compound or compounds alongside the customary excipients, such as (a) fillers and extenders, for example starches, lactose, sucrose, glucose, mannitol and silica, (b) binders, for example carboxymethylcellulose, alginates, gelatine and polyvinylpyrrolidone, (c) humectants, for example paraffin and (f) absorption accelerators, for example quaternary ammonium compounds, (g) wetting agents, for example cetyl alcohol and glycerol monostearate, (h) adsorbents, for example kaolin and bentonite, and (i) lubricants, for example talc, calcium stearate, magnesium stearate and solid polyethylene glycols, or mixtures of the substances listed under (a) to (i).

The tablets, dragees, capsules, pills and granules 15 can be provided with the customary coatings and shells, optionally containing opacifying agents, and can also be of such composition that they release the active compound or compounds only, or preferentially, in a certain part of the intestinal tract, optionally in a delayed manner, examples of embedding compositions which can be used being polymeric substances and waxes.

| Example of a tablet according to the invention | |
|---|---|
| Each tablet contains: | |
| Compound of Example 1 | 583.0 mg |
| Microcrystalline cellulose | 55.0 mg |
| Corn starch | 72.0 mg |
| Insoluble poly-(1-vinyl-2-pyrrolidone) | 30.0 mg |
| Highly disperse silicon dioxide | 5.0 mg |
| Magnesium stearate | 5.0 mg |
| | 750.0 mg |
| The lacquered shell contains: | |
| Poly-(O—hydroxypropyl-O—methyl)-cellulose 15 cp | 6.0 mg |
| Macrogol 4000 rec. INN polyethylene glycols DAB | 2.0 mg |
| Titanium-(IV) oxide | 2.0 mg |
| | 10.0 mg |

The active compound or compounds, optionally with one or more of the abovementioned excipients, can also be in microencapsulated form.

Suppositories can contain, in addition to the active compound or compounds, the customary water-soluble or water-insoluble excipients, for example polyethylene glycols, fats, for example cacao fat, and higher esters (for example $C_{14}$-alcohol with $C_{16}$-fatty acid), or mixtures of these substances.

Ointments, pastes, creams and gels can contain, in addition to the active compound or compounds, the customary excipients, for example animal and vegetable fats, waxes, paraffins, starch, tragacanth, cellulose derivatives, polyethylene glycols, silicones, bentonites, silica, talc and zinc oxide, or mixtures of these substances.

Powders and sprays can contain, in addition to the active compound or compounds, the customary excipients, for example lactose, talc, silica, aluminum hydroxide, calcium silicate and polyamide powder, or mixtures of these substances, and sprays can additionally contain the customary propellants, for example chlorofluorohydrocarbons.

Solutions and emulsions can contain, in addition to the active compound or compounds, the customary excipients, such as solvents, solubilizing agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, in particular cottonseed oil, groundnut oil, corn germ-oil, olive oil, castor oil and sesame oil, glycerol, glycerol formal, tetrahydrofurfuryl alcohol, polyethylene glycols and fatty acid esters of sorbitan, or mixtures of these substances.

For pereneteral administration, the solutions and emulsions can also be in a sterile form which is isotonic with blood.

Suspensions can contain, in addition to the active compound or compounds, the customary excipients, such as liquid diluents, for example water, ethyl alcohol or propylene glycol, suspending agents, for example ethoxylated isostearyl alcohols, polyoxyethylene sorbitol esters and sorbitan esters, microcrystalline cellulose, aluminum metahydroxide, bentonite, agar-agar and tragacanth, or mixtures of these substances.

The formulation forms mentioned can also contain colorants, preservatives and additives which improve the odor and flavor, for example peppermint oil and eucalyptus oil, and sweeteners, for example saccharin.

The therapeutically active compounds should preferably be present in the abovementioned pharmaceutical formulations in a concentration of about 0.1 to 99.5, preferably about 0.5 to 95% by weight of the total mixture.

The abovementioned pharmaceutical formulations can also contain other pharmaceutical active compounds in addition to the compounds according to the invention.

The abovementioned pharmaceutical formulations are prepared in the customary manner by known methods, for example by mixing the active compound or compounds with the excipient or excipients.

The active compounds or the pharmaceutical formulations can be administered locally, orally, parenterally, intraperitoneally and/or rectally, preferably orally or parenterally, such as intravenously or intramuscularly.

In general it has proved advantageous, both in human medicine and in veterinary medicine, to administer the active compound or compounds according to the invention in total amounts of about 0.5 to about 500, preferably 5 to 100 mg/kg of body weight every 24 hours, if appropriate in the form of several individual doses, to achieve the desired results. An individual dose contains the active compound or compounds according to the invention, preferably in amounts of about 1 to 250, in particular 3 to 60 mg/kg of body weight. However, it may be necessary to deviate from the dosages mentioned, and in particular to do so as a function of the nature and body weight of the subject to be treated, the nature and severity of the disease, the nature of the formulation and of the administration of the medicament, and the period or interval within which administration takes place.

Thus it can in some cases suffice to manage with less than the abovementioned amount of active compound, while in other cases the abovementioned amounts of active compound must be exceeded. The particular optimum dosage required and the type of administration of the active compounds can easily be determined by anyone skilled in the art on the basis of his expert knowledge.

The new compounds can be administered in the customary concentrations and formulations together with the feed or with feed formulations or with the drinking water. Infection by Gram-negative or Gram-positive bacteria can thereby be prevented, alleviated and/or cured, and a promotion in growth and an improvement in feed utilization can thereby be achieved.

The MIC values are given in the following Table 1.

| Strain | MIC mcg/ml Example No. | | Norfloxacin |
|---|---|---|---|
| | 1 | 3 | |
| E. coli Neumann | 0.06 | 0.06 | 0.06 |
| E. coli T 7 | ≦0.015 | 0.03 | 0.06 |

| | MIC mcg/ml | | |
|---|---|---|---|
| | Example No. | | |
| Strain | 1 | 3 | Norfloxacin |
| E. coli A 261 | ≦0.015 | 0.03 | 0.03 |
| Klebsiella 8085 | 0.03 | 0.06 | 0.125 |

Agar dilution test (Isosensitest medium); Denley multipoint inoculator

The following examples illustrate the invention

EXAMPLE A

7-Chloro-6-fluoro-1,4-dihydro-1-(1-methylcyclopropyl)-4-oxo-3-quinolinecarboxylic acid

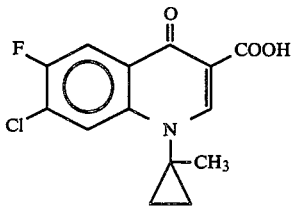

25.2 g of ethyl 2-(2,4-dichloro-5-fluorobenzoyl)-3-ethoxy-acrylate are introduced into 30 ml of EtOH. 5.7 g of 1-amino-1-methylcyclopropane in 30 ml of EtOH are added dropwise, with cooling. The mixture is stirred at room temperature for a further hour and 70 ml of ice-water are then added. The precipitate is filtered off with suction, washed with aqueous ethanol and dried.

Yield: 25.4 g of ethyl 2-(2,4-dichloro-5-fluorobenzoyl)-3-(1-methyl-cyclopropylamino)-acrylate of melting point 81°-82° C.

25 g of this compound are heated for two hours at 140° C. with 10 g of $K_2CO_3$ in 100 ml of dimethylformamide. The mixture is then poured hot onto ice and the precipitate is isolated and washed with water.

Yield: 21.1 g of ethyl 7-chloro-6-fluoro-1,4-dihydro-1-(1-methylcyclopropyl)-4-oxo-3-quinolinecarboxylate. Melting point 218°-19° C.

21.1 g of this compound are heated at 150° C. in a mixture of 75 ml of acetic acid, 57 ml of water and 7 ml of sulphuric acid for 1.5 hours. Thereafter, 120 ml of water are added dropwise, while cooling with ice, and the precipitate is filtered off with suction and washed with water.

Yield: 18.2 g of 7-chloro-6-fluoro-1,4-dihydro-1-(1-methylcyclopropyl)-4-oxo-3-quinolinecarboxylic acid of melting point 301°-3° C.

EXAMPLE B

7-Chloro-6-fluoro-1,4-dihydro-1-(2-methylcyclopropyl)-4-oxo-3-quinolinecarboxylic acid

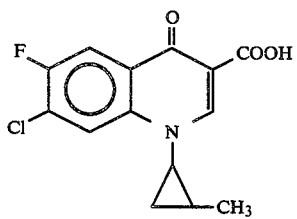

Ethyl 2-(2,4-dichloro-5-fluorobenzoyl)-3-ethoxyacrylate is reacted with 1-amino-2-methylcyclopropane analogously to Example A.

The following stages are obtained: 2-(2,4-dichloro-5-fluorobenzoyl)-3-(2-methylcyclopropyl)-aminoacrylate (yield 91%; melting point 80°-85 C.), ethyl 7-chloro-6-fluoro-1,4-dihydro-1-(2-methylcyclopropyl)-4-oxo-3-quinolinecarboxylate (yield 84%; melting point 185°-8° C.) and 7-chloro-6-fluoro-1,4-dihydro-1-(2-methylcyclopropyl)4-oxo-3-quinolinecarboxylic acid (yield 79%; melting point 218°-20° C.)

EXAMPLE C 6,7,8-Trifluoro-1-(2,2-difluorocyclopropyl)-1,4-dihydro-4oxo-3-quinolinecarboxylic acid.

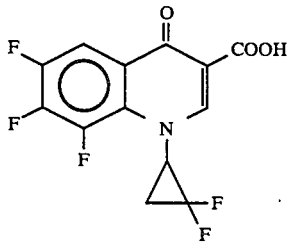

6 g of ethyl 3-ethoxy-2-(2,3,4,5-tetrafluorobenzoyl)-acrylate (known) in 30 ml of $CH_2Cl_2$ and 2.4 g of 1-amino-2,2-difluorocyclopropane hydrochloride in 12 ml of water are taken together, while cooling with ice. A solution of 1.6 g of $NaHCO_3$ in 20 ml of water is added dropwise, with intensive stirring. The mixture is subsequently stirred for 2 hours, the phases are separated and the organic phase is washed with water, dried and concentrated. 6.2 g of crude 2-(2,3,4,5-tetrafluorobenzoyl)-3-(2,2)difluorocyclopropylamino)-acrylate remain.

Yield: 92%

3.7 % of this compound are boiled with 0.7 g of NaF in 22 ml of dimethylformamide for 2 hours. Thereafter, the mixture is poured onto ice and the product which has precipitated is isolated.

Yield: 3.0 g (86%) of ethyl 6,7,8-trifluoro-1-(2,2-difluorocyclopropyl)-1,4-dihydro-4-oxo-3-quinolinecarboxylate Melting point: 118°-20° C.

4.5 g of this compound are heated at 150° (bath) in a mixture of 14 ml of AcOH, 11 ml of water and 1.3 ml of sulphuric acid for 2 hours. After cooling, the mixture is poured onto ice and the precipitate is isolated.

Yield: 3.0 g of 6,7,8-trifluoro-1-(2,2-difluorocyclopropyl)-1,4-dihydro-4-oxo-3-quinolinecarboxylic acid (72%)

Melting point: 238°-40° (decomposition)

EXAMPLE 1

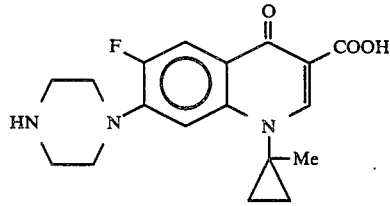

3 g of Example A and 2.6 g of anhydrous piperazine are boiled in 75 ml of pyridine for 8 hours. Thereafter, the mixture is concentrated in vacuo. The residue is stirred with 45 ml of water and the pH is brought to 5 with HCl. The precipitate is filtered off with suction, washed with water and dried at 100° C. in vacuo.

Yield: 2.1 g of 6-fluoro-1,4-dihydro-1-(1-methylcyclopropyl)-4-oxo-7-(1-piperazinyl)-3-quinolinecarboxylic acid Melting point: 269°–71° C.

The following 7-fluoro-1,4-dihydro-1-(1-methylcyclopropyl)- 4-oxo-3-quinolinecarboxylic acids substitutes in the 7-position are obtained analogously to Example 1:

| Example | \N/ | Melting point |
|---|---|---|
| 2 | CH₃—N\_/N— | 248–9° C. |
| 3 | H—N\_/N— (CH₃) | 186–8° C. |
| 4 | Et—N\_/N— | 234–36° C. |
| 5 | HO—CH₂CH₂—N\_/N— | 198–203° C. |
| 6 | Ph-CH(-N\_/N-H) | 218–20° C. |
| 7 | piperidinyl-N— | 292–94° C. |

EXAMPLE 8

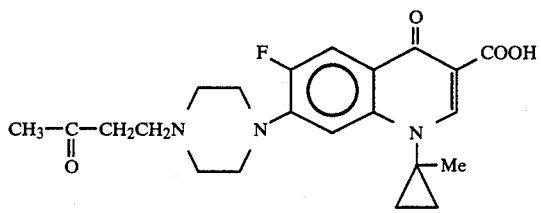

3.4 g of the product from Example 1 and 3.9 g of methyl vinyl ketone are boiled in 25 ml of ethanol for 6 hours. The mixture is filtered hot and, after cooling, the precipitate is filtered off with suction.

Yield: 3.2 g of 7-fluoro-1, 4-dihydro-4-oxo-7-[4(3-oxobutyl)-1-piperazinyl]-3-quinolinecarboxylic acid Melting point: 158°–60° C.

EXAMPLE 9

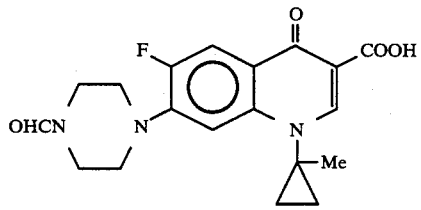

3.1 g of the product from Example 1 and 3 ml of formic acid are boiled in 30 ml of dimethylformamide for 8 hours. After cooling, the precipitate is filtered off with suction, washed with water and methanol and dried.

Yield: 2.0 g of 6-fluoro-7-(4-formyl-1-piperazinyl)-1,4-dihydro-4-oxo-3-quinolinecarboxylic acid Melting point: 297°–99° (decomposition)

EXAMPLE 10

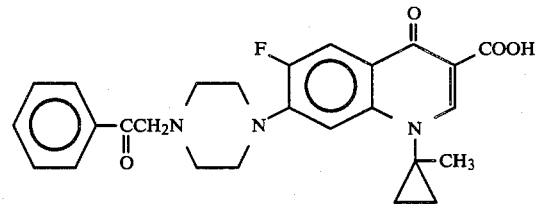

3.4 g of the product from Example 1, 2.3 g of ω-chloroacetophenone and 2.1 g of triethylamine are boiled in 50 ml of ethanol for 9 hours. The mixture is concentrated in vacuo and the residue is stirred with water. The precipitate is isolated, dried and dissolved in toluene. The product is precipitated by addition of light benzine.

Yield: 1 g of 6-fluoro-1,4-dihydro-1-(1-methylcyclopropyl)-4-oxo-7-[4-(2-oxo-2-phenyl-ethyl)-1-piperazinyl]-3-quinolinecarboxylic acid Melting point: 215°–18°

EXAMPLE 11

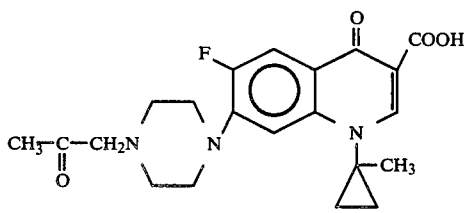

3.4 g of the product from Example 1, 3.9 g of chloroacetone and 5.8 ml of triethylamine are boiled in 50 ml of ethanol for 6 hours. The mixture is then concentrated, the residue is dissolved in MeOH and the product is precipitated with water.

Yield: 2.0 g of 7-fluoro-1,4-dihydro-1-(1-methylcyclopropyl)-4-oxo-7-[4-(2-oxo-propyl)-1-piperazinyl-3-quinolinecarboxylic acid Melting point: 188°–90° (decomposition)

EXAMPLE 12

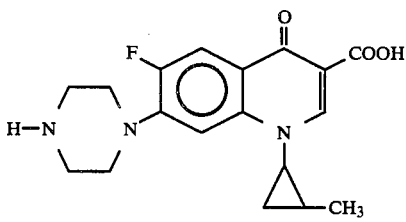

3 g of Example B and 2.6 g of piperazine are boiled in 75 ml of pyridine for 8 hours. The mixture is concentrated and the residue is stirred with 45 ml of water. The pH is brought to 5 with HCl. The precipitate is filtered off with suction, washed with water and dried. 1.8 g of 6-fluoro-1, 4-dihydro-1-(2-methylcyclopropyl)-4-oxo-7-(1piperazinyl)-3-quinolinecarboxylic acid are obtained.

Melting point: 110°–20° C.

The following 7-fluoro-1, 4-dihydro-1-(2-methylcyclopropyl)-4-oxo-3-quinolinecarboxylic acids substituted in the 7-position are obtained analogously to Example 12:

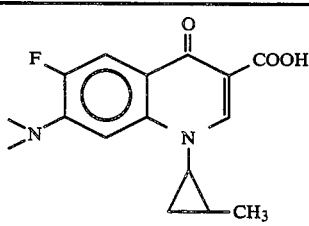

| Example | >N< | Melting point |
|---|---|---|
| 13 | 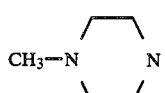 | 204-7° |

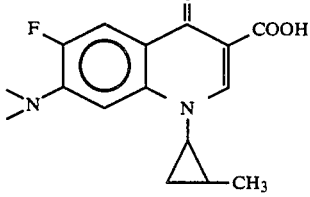

| Example | >N< | Melting point |
|---|---|---|
| 14 | 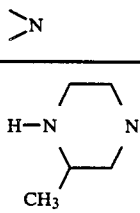 | 210-12° |
| 15 | 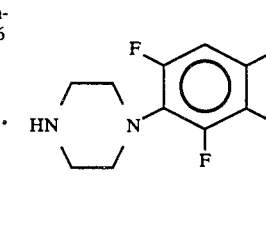 | 188-90° |

Example 16

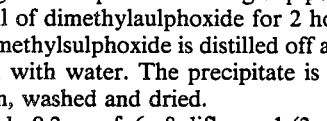

0.4 g of Example C and 0.54 g of piperazine are boiled in 2 ml of dimethylaulphoxide for 2 hours. Thereafter, the dimethylsulphoxide is distilled off and the residue is stirred with water. The precipitate is filtered off with suction, washed and dried.

Yield: 0.2 g of 6, 8-difluoro-1-(2, 2-difluorocyclopropyl)1,4-dihydro-4-oxo-7-(1-piperazinyl)-3-quinolinecarboxylic acid Melting point: 204°–6° C.

The following 6,8-difluoro-1-(2,2-difluorocyclopropyl)-1,4-dihydro-4-oxo-3-quinolinecarboxylic acids substituted in the 7-position are obtained analogously to

EXAMPLE 16:

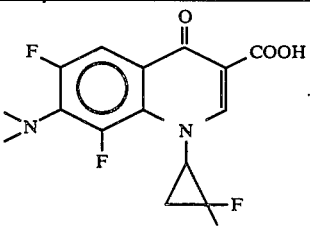

| Example | >N< | Melting point |
|---|---|---|
| 17 | 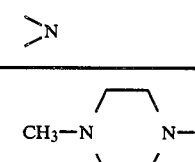 | 302-4° (decomposition) |

-continued

[Structure: 6-fluoro-7-(dimethylamino)-8-fluoro-1-(2,2-difluorocyclopropyl)-4-oxo-quinoline-3-carboxylic acid]

| Example >N | | Melting point |
|---|---|---|
| 18 | HN⟩—⟨N— with CH₃ substituent (2-methylpiperazine) | 278–80° (decomposition) |
| 19 | CH₃CH₂—N⟩—⟨N— (4-ethylpiperazine) | 310° (decomposition) |

It will be understood that the specification and examples are illustrative but not limitative of the present invention and that other embodiments within the spirit and scope of the invention will suggest themselves to those skilled in the art.

What is claimed is:

1. A 7-amino-1-(substituted cyclopropyl)-1,4-dihydro-4-oxo-3-quinolinecarboxylic acid of the formula

[Structure: general formula with X¹, X², R₄, R₅, N, and cyclopropyl with R₁, R₂, R₃ substituents, COOH at 3-position]

in which $X^1$ and $X^2$ can be identical of different and represent hydrogen or halogen, $R_1$, $R_2$ and $R_3$ represent hydrogen, methyl, chlorine or fluorine, the radicals $R_1$–$R_3$ never all being identical, and $R_4$ and $R_5$, together with the nitrogen atom to which they are bonded, form a morpholine, piperidine, thiomorpholine, pyrrolidine, piperazine, N-methylpiperazine, N-ethylpiperazine, N-(2-hydroxyethyl)-piperazine, n-formylpiperazine, 2-methyl-piperazine, 1,2-dimethylpiperazine, cis- and trans-2,5-dimethylpiperazine, cis- and trans-2,6-dimethylpiperazine, 2-ethylpiperazine, 2-propylpiperazine, 2-iosopropylpiperazine, 2-isobutylpiperazine, 2-piperazinone, 1-methyl-2-piperazinone, 1-ethyl-2-piperazinone, 2-cyclohexylpiperazine, 2-phenylpiperazine, 2-(4-chlorophenyl)-piperazine, 2-(4-fluorophenyl)piperazine, 2-(4-bromophenyl)-piperazine, 2-(4-methylphenyl)-piperazine, 2-4(biphenyl)piperazine, 2-(4-methoxophenyl)-piperazine, 2-(4-benzyloxyphenyl)-piperazine, -(4-hydroxyphenyl)-piperazine, 2-(4-nitrophenyl)-piperazine, 2-(3-nitrophenyl)-piperazine, 2-(4-piperadinophenyl)-piperazine, 2-3,4-dimethoxyphenyl-piperazine, 2-(3,4,5-trimethoxyphenyl)-piperazine, 2-(3,4-dimethoxy-6-methyl)-piperazine, 2-(2-thienyl)-piperazine or 3-amino-pyrrolidine radical.

2. A 7-amino-(substituted cyclopropyl)-1, 4-dihydro-4-oxo-3-quinolinecarboxylic acid according to claim 1, in which $X^1$ and $X^2$ can be identical or different and represent hydrogen, chlorine or fluorine.

3. A 7-amino-1-(substituted cyclopropyl)-1,4-dihydro-4-oxo-3-quinolinecarboxylic acid according to claim 1 and selected from the group consisting of 8-chloro-6-fluoro-1,4-dihydro-1-(1-methylcyclopropyl)-4-oxo-7-(1-piperazinyl)-3-quinolinecarboxylic acid, 6-chloro-8-fluoro-1,4-dihydro-1-(1-methylcyclopropyl)-4-oxo-7-(1-piperazinyl)-3-quinolinecarboxylic acid, 6-chloro-8-fluoro-1-(2,2-difluorocyclopropyl)-1,4-dihydro-4-oxo-7-(1-piperazinyl)-3-quinolinecarboxylic acid, 6,8-difluoro-1-(2-fluorocyclopropyl)-1,4-dihydro-4-oxo-7-(1-piperazinyl)-3quinolinecarboxylic acid, 1-(2,2-dichlorocyclopropyl)-6,8-difluoro-1,4-dihydro-4-oxo-7-(1-piperazinyl)-3-quinoline-carboxylic acid, 8-chloro-6-fluoro-1,4-dihydro-1-(2-methylcyclopropyl)-7-(3-methyl-1-piperazinyl)-4-oxo-3-quinolinecarboxylic acid, 8-chloro-6-fluoro-1,4-dihydro-1-(1-methylcyclopropyl)-7-(3-methyl-1-piperazinyl)-4-oxo-3-quinolinecarboxylic acid, 6-chloro-8-fluoro-1-(2-fluorocyclopropyl)-1,4-dihydro-4-oxo-7-(1-piperazinyl)-3-quinolinecarboxylic acid, 1-(2-chlorocyclopropyl)-6,8-difluoro-1,4-dihydro-4-oxo-7-(1-piperazinyl)-3-quinolinecarboxylic acid, 6,8-difluoro-1,4-dihydro-1-(1-methylcyclopropyl)-4-oxo-7-(3-phenyl-1-piperazinyl)-3-quinolinecarboxylic acid, 8-chloro-6-fluoro-1,4-dihydro-1-(1-methylcyclopropyl)-4-oxo-7-(3-phenyl-1-piperazinyl)-3-quinolinecarboxylic acid, 6,8-difluoro-1-(2,2-difluorocyclopropyl)-1,4-dihydro-4-oxo-7-(3-phenyl-1-piperazinyl)-3-quinolinecarboxylic acid, 8-chloro-6-fluoro-1-(2,2-difluorocyclopropyl)-1,4-dihydro-7-(4-methyl-1-piperazinyl)-4-oxo-3-quinolinecarboxylic acid, 6-chloro-8-fluoro-1-(2,2-difluorocyclopropyl)-1,4-dihydro-7-(4-methyl-1-piperazinyl)-4-oxo-3-quinolinecarboxylic acid, 6-chloro-8-fluoro-1-(2,2-difluorocyclopropyl)-1,4-dyhydro-7-(4-methyl-1-piperazinyl)-4-oxo-3-quinolinecarboxylic acid, 7-(4-acetyl-1-piperazinyl)-6,8-difluoro-1,4-dihydro-1-(1-methylcyclopropyl)-4-oxo-3-quinolinecarboxylic acid, 6,8-difluoro-1,4-dihydro-4-oxo-7-[4-(3-oxo-butyl)-1-piperazinyl]-3-quinolinecarboxylic acid and 1-(2,2-dichlorocyclopropyl)-6-fluoro-1,4-dihydro-4-oxo-7-(1-piperazinyl)-3-quinolinecarboxylic acid.

4. A compound according to claim 1, wherein such compound is 6-fluoro-1,4-dihydro-1-(1-methylcyclopropyl)-4-oxo-7-(1-piperazinyl)-3-quinolinecarboxylic acid of the formula

[Structure: 6-fluoro-7-(piperazin-1-yl)-1-(1-methylcyclopropyl)-4-oxo-quinoline-3-carboxylic acid]

5. A compound according to claim 1, wherein such compound is 6-fluoro-1,4-dihydro-1-(1-methylcyclopropyl)-4-oxo-7-(4-methyl-1-piperazinyl)-3-quinolinecarboxylic acid of the formula

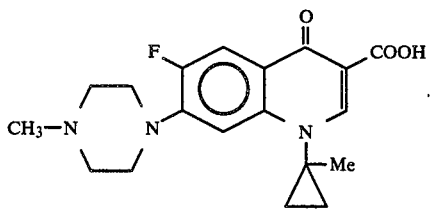

6. A compound according to claim 1, wherein such compound is 6-fluoro-1,4-dihydro-1-(1-methylcyclopropyl)-4-oxo-7-(3-methyl-1-piperazinyl)-3-quinolinecarboxylic acid of the formula

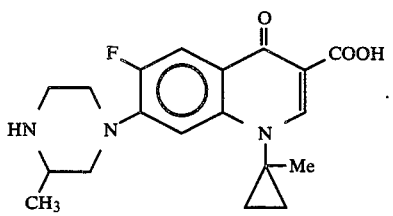

7. A compound according to claim 1, wherein such compound is 6,8-difluoro-1-(2,2-difluorocyclopropyl)-1,4-dihydro-4-oxo-7-(1-piperazinyl)-3-quinolinecarboxylic acid of the formula

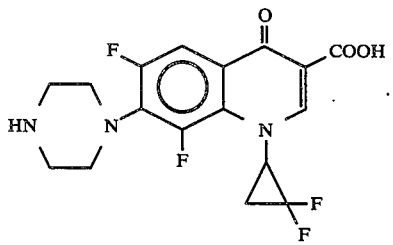

8. A compound according to claim 1, wherein such compound is 6,8-difluoro-1-(2,2-difluorocyclopropyl)-1,4-dihydro-4-oxo-7-(4-methyl-1-piperazinyl)-3-quinolinecarboxylic acid of the formula

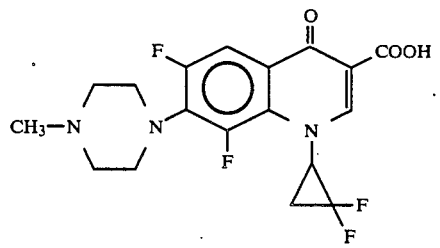

9. A compound according to claim 1, wherein such compound is 6,8-difluoro-1-(2,2-difluorocyclopropyl)-1,4-dihydro-4-oxo-7-(3-methyl-1-piperazinyl)-3-quinolinecarboxylic acid of the formula

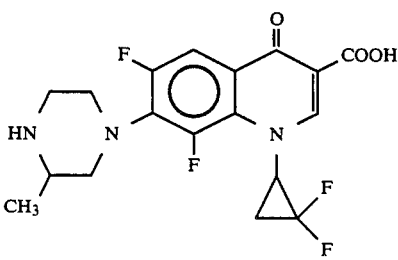

10. An antibacterial composition comprising an antibacterially effective amount of a compound according to claim 1 in admixture with a diluent.

11. A unit dose of a composition according to claim 1 in the form of a tablet, capsule or ampule.

12. A method of combating bacteria which comprises applying to a bacteria habitat or to a patient infected by or to be protected against such bacteria an antibacterially effective amount of a compound according to claim 1.

13. The method according to claim 12, wherein such compound is
6-fluoro-1,4-dihydro-1-(1-methylcyclopropyl)-4-oxo-7-(1-piperazinyl)-3-quinolinecarboxylic acid,
6-fluoro-1,4-dihydro-1-(1-methylcyclopropyl)-4-oxo-7-(4-methyl-1-piperazinyl)-3-quinolinecarboxylic acid;
6-fluoro-1,4-dihydro-1-(1-methylcyclopropyl)-4-oxo-7-(3-methyl-1-piperazinyl)-3-quinolinecarboxylic acid,
6,8-difluoro-1-(2,2-difluorocyclopropyl)-1,4-dihydro-4-oxo-7-(1-piperazinyl)-3-quinolinecarboxylic acid,
6,8-difluoro-1-(2,2-difluorocyclopropyl)-1,4-dihydro-4-oxo-7-(4-methyl-1-piperazinyl)-3-quinolinecarboxylic acid or
6-8-difluoro-1-(2,2-difluorocyclopropyl)-1,4-dihydro-4-oxo-7-(3-methyl-1-piperazinyl)-3-quinolinecarboxylic acid.

* * * * *

UNITED STATES PATENT AND TRADEMARK OFFICE
CERTIFICATE OF CORRECTION

PATENT NO. : 4,705,788

DATED : Nov. 10, 1987

INVENTOR(S) : Schriewer et al.

Page 1 of 2

It is certified that error appears in the above-identified patent and that said Letters Patent is hereby corrected as shown below:

| | |
|---|---|
| Col. 7, line 57 | Leave a space between "point" and "66" |
| Col. 8, line 40 | Insert --been-- after "has" |
| Col. 9, line 61 | Insert -- - -- after "3" |
| Col. 10, line 15 | Delete "L" and insert --[-- after "bicyclo" and insert --]-- after "2" in the third instance |
| Col. 10, line 16 | Delete "L" and insert --(-- after "bicyclo" and delete "j" and insert --)-- after "0" |
| Col. 10, line 41 | Delete "1" and insert --[-- before "2" in the first instance |
| Col. 11, line 41 | Delete "14" and substitute --[4-- and delete "piperazinylj" and substitute --piperazinyl]-- |
| Col. 11, line 57 | Insert --,-- after "fibers" |
| Col. 13, line 64 | Correct spelling of --parenteral-- |
| Col. 15, line 14 | Insert -- - -- after "4" |
| Col. 15, line 28 | Delete "EtoH" and substitute --EtOH-- |
| Col. 15, line 29 | Delete "EtoH" and substitute --EtOH-- |
| Col. 15, line 57 | Insert -- - -- after "4" |
| Col. 16, line 15 | Insert -- - -- after "4" |
| Col. 16, line 29 | Insert -- - -- between "1" and "amino" |
| Col. 16, line 37 | Delete ")" after "2" in second instance and insert -- - -- |
| Col. 19, line 20 | Insert --]-- after "piperazinyl" |
| Col. 19, line 43 | Insert -- - -- before "piperazinyl" |
| Col. 20, line 38 | Correct spelling of --dimethylsulphoxide-- |
| Col. 21, line 57 | Delete "n" and insert --N-- |

UNITED STATES PATENT AND TRADEMARK OFFICE
CERTIFICATE OF CORRECTION

PATENT NO. : 4,705,788

DATED : Nov. 10, 1987

INVENTOR(S) : Schriewer et al.

It is certified that error appears in the above-identified patent and that said Letters Patent is hereby corrected as shown below:

| | |
|---|---|
| Col. 21, line 65 | Insert -- - -- after "fluorophenyl)" |
| Col. 21, line 67 | Insert -- - -- after "biphenyl)" |
| Col. 22, line 3 | Insert --(-- after "2-" |
| Col. 22, line 7 | Insert -- -1 -- after "amino" |
| Col. 22, line 22 | Insert -- - -- after "3" |
| Col. 22, line 44 | Delete from "6" to "acid on line 46 |
| Col. 22, line 43 | Insert -- - -- after "17". |

Signed and Sealed this

Nineteenth Day of July, 1988

Attest:

DONALD J. QUIGG

Attesting Officer

Commissioner of Patents and Trademarks